(12) United States Patent
Myatt

(10) Patent No.: US 9,358,201 B2
(45) Date of Patent: *Jun. 7, 2016

(54) HAIR COLOURING METHODS AND KITS THEREOF

(71) Applicant: The Procter & Gamble Company, Cincinnati, OH (US)

(72) Inventor: Graham John Myatt, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/465,409

(22) Filed: Aug. 21, 2014

(65) Prior Publication Data

US 2015/0053230 A1    Feb. 26, 2015

Related U.S. Application Data

(60) Provisional application No. 61/869,199, filed on Aug. 23, 2013.

(51) Int. Cl.

| | |
|---|---|
| *A61Q 5/10* | (2006.01) |
| *A61K 8/67* | (2006.01) |
| *A61K 8/19* | (2006.01) |
| *A61K 8/20* | (2006.01) |
| *A61K 8/23* | (2006.01) |
| *A61K 8/24* | (2006.01) |
| *A61K 8/25* | (2006.01) |
| *A61K 8/36* | (2006.01) |
| *A61K 8/365* | (2006.01) |
| *A61K 8/40* | (2006.01) |
| *A61K 8/41* | (2006.01) |
| *A61K 8/55* | (2006.01) |
| *A61Q 5/06* | (2006.01) |

(52) U.S. Cl.
CPC . *A61K 8/676* (2013.01); *A61K 8/19* (2013.01); *A61K 8/20* (2013.01); *A61K 8/23* (2013.01); *A61K 8/24* (2013.01); *A61K 8/25* (2013.01); *A61K 8/36* (2013.01); *A61K 8/365* (2013.01); *A61K 8/40* (2013.01); *A61K 8/415* (2013.01); *A61K 8/55* (2013.01); *A61Q 5/065* (2013.01); *A61Q 5/10* (2013.01); *A61K 2800/20* (2013.01); *A61K 2800/88* (2013.01); *A61K 2800/884* (2013.01)

(58) Field of Classification Search
CPC ..... A61Q 5/10; A61Q 5/065; A61K 2800/20; A61K 2800/88; A61K 2800/884
USPC ............................................. 8/405; 132/132
See application file for complete search history.

(56) References Cited

U.S. PATENT DOCUMENTS

| | | |
|---|---|---|
| 2,528,378 A | 10/1950 | Mannheimer |
| 2,781,354 A | 2/1957 | Mannheimer |
| 6,099,828 A | 8/2000 | Kajino |
| 6,743,264 B2 * | 6/2004 | Sarojini ................. A61K 8/415 8/405 |
| 6,835,018 B2 | 12/2004 | Miczewski et al. |
| 7,875,269 B2 | 1/2011 | Bureiko |
| 8,632,611 B2 | 1/2014 | Agostino |
| 2008/0178399 A1 | 7/2008 | Franco |

FOREIGN PATENT DOCUMENTS

| | | | |
|---|---|---|---|
| FR | 2953397 | B1 | 1/2012 |
| JP | 08333224 | A | 12/1996 |
| JP | 2010248103 | A | 11/2010 |

OTHER PUBLICATIONS

U.S. Appl. No. 14/465,314, filed Aug. 21, 2014, Bonauer.
U.S. Appl. No. 14/465,335, filed Aug. 21, 2014, Bonauer.
U.S. Appl. No. 14/465,384, filed Aug. 21, 2014, Bonauer.
U.S. Appl. No. 14/465,434, filed Aug. 21, 2014, Bonauer.
U.S. Appl. No. 14/465,478, filed Aug. 21, 2014, Berlepsch.
U.S. Appl. No. 14/465,488, filed Aug. 21, 2014, Schofield.

* cited by examiner

*Primary Examiner* — Eisa Elhilo
(74) *Attorney, Agent, or Firm* — James T. Fondriest

(57) ABSTRACT

Method for coloring hair wherein a first hair coloring composition comprising one or more direct dyes is applied to a first region the hair and a second hair coloring composition is applied to a second region of the hair, wherein the pH of the second composition is lower or higher than the pH of the first composition.

19 Claims, No Drawings

HAIR COLOURING METHODS AND KITS THEREOF

FIELD OF THE INVENTION

The invention relates to a method of hair colouring using direct dyes and kits thereof.

BACKGROUND OF THE INVENTION

For consumers who have previously coloured their hair, the colour and condition of the hair is not homogenous along the entire length. The hair strands will comprise root virgin hair or new growth hair which has not been previously coloured and conversely at the tips hair which has experienced one or multiple hair colouring treatments. The tips of the hair are typically the most damaged portions of the hair and are characterised by an overly deposition of dyes or over-bleaching due to previous oxidative or non-oxidative hair colorations. The intermediate hair length is typically a medium between these two extreme conditions. The problem with current retail hair colour products, e.g. hair colour products comprising direct dyes is that they do not take into account the differences of properties between the different portions of the hair. It is rather challenging even for experienced home colour users to control the dye deposition provided by a retail hair colour product comprising direct dyes in order to not overly deposit direct dyes on hair lengths and tips since the instructions provided in hair colour retail kits are typically imprecise, often not followed and the results achieved are not comparable with those from a salon stylist. The overall colour appearance is typically not as homogeneous as that provided by a salon stylist.

Therefore, there is a need to provide a simple method as well as a simple retail kit for colouring hair with hair colouring compositions comprising direct dyes which gives the user the possibility of obtaining a different hair colour effect on different portions of the hair, for example a different colour effect on hair roots vs. hair lengths and tips to provide a smooth root-to-tip transition on hair which has been previously coloured.

SUMMARY OF THE INVENTION

The present invention relates to a method for colouring hair comprising the steps of:
i) providing a first hair colouring composition and a second hair colouring composition, wherein each of the first and second compositions comprises one or more direct dyes and the pH of the second hair colouring composition is lower or higher than the pH of the first hair colouring composition;
ii) applying a portion or all of the first hair colouring composition to a first region of the hair;
iii) applying a portion or all of the second hair colouring composition to a second region of the hair.

The present invention also relates to a hair colouring kit comprising a first hair colouring composition and a second hair colouring composition, wherein each of the first and second compositions comprises one or more direct dyes and the pH of the second hair colouring composition is lower or higher than the pH of the first hair colouring composition.

Furthermore, the present invention also relates to a hair colouring kit comprising a first hair colouring composition comprising one or more direct dyes and a pH modifying agent, wherein the pH modifying agent is a pH reducing agent or a pH increasing agent.

DETAILED DESCRIPTION OF THE INVENTION

While the specification concludes with claims, which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibres. Mammalian, preferably human hair is preferred. However wool, fur and other keratin containing fibres are suitable substrates for the compositions according to the present invention. The terms "root", "hair roots", "root hair line" and "virgin hair" all refer to hair which has not been previously treated with a hair colouring or bleaching composition.

By "hair colouring" composition it is meant a composition suitable for changing the color of hair. The hair colouring composition comprises direct dyes but may also comprise direct dyes in combinations with oxidative dye precursors.

In the preferred embodiment according to the present invention, the hair colouring compositions are applied to hair which has already been previously coloured with hair colouring compositions comprising direct dyes and/or oxidative dye precursors. In such a case, the terms "root", "hair roots", "root hair line" and "virgin hair" all refer to the portion of hair having grown, since the last hair colouration, said portion of hair being virgin, i.e. naturally-coloured and the terms "hair lengths and tips" refer to the remaining portion of hair having been already previously coloured.

By "liquid" it is meant liquid at 25° C. and at atmospheric pressure (760 mmHg).

By "solid" it is meant solid at 25° C. and at atmospheric pressure (760 mmHg).

All percentages are by weight of the total composition unless specifically stated otherwise. All ratios are weight ratios unless specifically stated otherwise.

Method for Colouring Hair

The present invention relates to a method for colouring hair as stated hereinbefore.

The method may further comprise the step iv) of rinsing the hair.

The difference of pH between the first composition and the second composition may be at least 0.1 or at least 0.25 or at least 0.5 or at least 1.

The second region of the hair to which a portion or all of the second hair colouring composition is applied may be different from the first region of the hair to which a portion or all of the first hair colouring composition is applied. The first region may be the hair roots and the second region may be the hair lengths and tips. Alternatively, the first region may be the hair lengths and tips and the second region may be the hair roots.

In step iv) of the method, the hair may be rinsed with water and/or shampoo. After rinsing, they may be further dried and styled as usual. A conditioner composition may be applied to the hair after rinsing, preferably prior to drying and styling.

The present description is not limited to the embodiments wherein only two different hair colouring compositions comprising direct dyes are applied to the hair, wherein the second hair colouring composition has a lower or higher pH than the first hair colouring composition. It may be envisaged to apply more than two different hair colouring compositions to the hair wherein each time the pH of the next composition is lower or higher than the pH of the previous composition.

The direct dyes comprised in the first and second compositions may be the same or different. The concentration of direct dyes comprised in the first and second compositions may be the same or different.

The direct dyes may be selected from cationic direct dyes and/or anionic direct dyes.

The cationic direct dyes may be selected from the group consisting of Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Violet 2, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide, and mixtures thereof.

The anionic direct dyes may be selected from the group consisting of Acid Yellow 1, Acid Orange 3, Acid Black 1, Acid Black 52, Acid Orange 7, Acid Red 33, Acid Yellow 23, Acid Blue 9, Acid Violet 43, Acid Blue 62, Acid Blue 25, Acid Red 4, Acid Red 92, Acid Yellow 3, Acid Red 18, Acid Red 52, Acid Green 25, and mixtures thereof.

pH Modifying Agent

In step ii) of the method according to the present invention, a first portion of the first composition may be applied to the first region of the hair and a second portion of the first composition may be retained and the method may further comprise the step of adding a pH modifying agent to the second portion of the first composition to obtain the second composition.

The pH modifying agent may be provided as a solid or a liquid.

In the embodiments wherein the pH modifying agent is provided as a liquid, it may be a solution, an emulsion or a suspension. In these embodiments, the solvent used to form the solution, emulsion or suspension may be water.

In the embodiments, wherein the pH modifying agent is provided as a liquid, the pH modifying agent:second portion of the first composition mixing ratio may be less than 1:4, or less than 1:10

In the embodiments wherein the pH modifying agent is provided as a liquid the pH modifying agent:second portion of the first composition mixing ratio may be of 1:4 or more, or 1:4 to 25:1, or 1:4 to 20:1 or 1:4 to 10:1 or 2:1 to 5:1. Whilst not wishing to be bound by theory, it is believed that with such a mixing ratio the pH modifying agent will also act as a diluter which will reduce the overall concentration of direct dyes and will contribute to the reduction of the deposition of direct dyes on hair.

pH Reducing Agent

The pH of the second hair colouring composition may be lower than the pH of the first hair colouring composition and the pH modifying agent may a pH reducing agent.

According to the present invention, a pH reducing agent is typically an acid which is added to a composition to lower the pH of the composition.

Whilst not wishing to be bound by theory, it is believed that when the pH of a hair colouring composition comprising one or more direct dyes which are cationic direct dyes and/or anionic direct dyes is lowered, the density of negative charges on hair decreases and therefore the deposition of cationic direct dyes will be reduced, whereas the deposition of anionic direct dyes will be increased. Therefore, it is possible for the user to have a better control on the deposition of direct dyes on hair.

The pH of the first hair colouring composition may be from 6 to 10 or from 8 to 10 and the pH of the second hair colouring composition may be from 2 to 8 or from 2 to 4.

The pH reducing agent may be selected from the group consisting of acetic acid, acetyl mandelic acid, adipic acid, aluminum lactate, aluminum triformate, ammonium lactate, ammonium molybdate, ammonium nitrate, ammonium thiocyanate, ammonium vanadate, ascorbic acid, azelaic acid, babassu acid, bakuhan, benzilic acid, bismuth citrate, boric acid, calcium citrate, calcium dihydrogen phosphate, calcium phosphate, citric acid, diammonium citrate, dioleyl phosphate, disodium pyrophosphate, fumaric acid, galacturonic acid, glucoheptonic acid, glucuronic acid, glutaric acid, glycine, glycolic acid, glyoxylic acid, hydrobromic acid, hydrochloric acid, hydroxyethylpiperazine ethane sulfonic acid, isobutyric acid, lactic acid, lactobionic acid, magnesium glycinate, magnesium lactate, maleic acid, malic acid, malonic acid, maltobionic acid, metaphosphoric acid, monosodium citrate, mudstone powder, phenolsulfonphthalein, phenyl mercuric borate, phosphoric acid, phosphorus pentoxide, potassium bicarbonate, potassium biphthalate, potassium magnesium aspartate, potassium sodium tartrate, potassium tartrate, propane tricarboxylic acid, quinic acid, ribonic acid, sebacic acid, sodium aspartate, sodium bisulfate, sodium borate, sodium butoxyethoxy acetate, sodium calcium boron phosphate, sodium calcium copper phosphate, sodium calcium zinc phosphate, sodium citrate, sodium glycolate, sodium lactate, sodium phosphate, sodium succinate, succinic acid, sulfuric acid, tartaric acid, taurine, tea-hydroiodide, trisodium sulfosuccinate, triticum vulgare protein, triticum vulgare seed extract, uric acid, zinc hexametaphosphate, and mixtures thereof. The pH reducing agent may be selected from the group consisting of citric acid, phosphoric acid, salicylic acid, etidronic acid, acetic acid, ascorbic acid, hydrochloric acid, sulfuric acid, and mixtures thereof.

pH Increasing Agent

The pH of the second hair colouring composition may be higher than the pH of the first hair colouring composition and the pH modifying agent may be a pH increasing agent.

According to the present invention, a pH increasing agent is typically a base which is added to a composition to increase the pH of the composition.

Whilst not wishing to be bound by theory, it is believed that when the pH of a hair colouring composition comprising one or more direct dyes which are cationic direct dyes and/or anionic direct dyes is increased, the density of negative charges on hair increases and therefore the deposition of anionic direct dyes will be reduced, whereas the deposition of cationic direct dyes will be increased. Therefore, it is possible for the user to have a better control on the deposition of direct dyes on hair.

The pH of the first hair colouring composition may be from 2 to 8, or from 2 to 4 and the pH of the second hair colouring composition may be from 6 to 10 or from 8 to 10.

The pH increasing agent may be selected from the group consisting of 1,6-hexanediamine, 2-aminobutanol, aminoethyl propanediol, aminomethyl propanediol, aminomethyl propanol, aminopropanediol, ammonia, ammonium bicarbonate, ammonium carbamate, ammonium carbonate, ammonium chloride, ammonium glycolate, ammonium hydroxide, ammonium phosphate, bis-hydroxyethyl tromethamine, butyl diethanolamine, calcium carbonate, calcium glycinate, calcium hydroxide, calcium oxide, copper glycinate, diammonium phosphate, dibutyl ethanolamine, diethyl ethanolamine, dimethyl isopropanolamine, dimethyl mea, dipotassium phosphate, disodium fumarate, disodium phosphate, disodium tartrate, ethanolamine, ethyl ethanolamine, guanidine carbonate, guanidine hcl, imidazole, isopropanolamine, isopropylamine, lithium carbonate, lithium hydroxide, magnesium hydroxide, magnesium oxide, methylethanolamine, pentapotassium triphosphate, pentasodium triphosphate, phenolsulfonphthalein, phenyl mercuric borate, potassium borate, potassium carbonate, potassium citrate, potassium hydroxide, potassium oxide, potassium phosphate, sesquiethoxytriethanolamine, sodium acetate, sodium aluminate, sodium aluminum lactate, sodium bicarbonate, sodium carbonate, sodium formate, sodium fumarate, sodium humate, sodium hydroxide, sodium metaphosphate, sodium metasilicate, sodium oxide, sodium sesquicarbonate, sodium silicate, sodium trimetaphosphate, strontium hydroxide,teadiricinoleate/ipdi copolymer, tetrahydroxyethyl ethylenediamine, tetrapotassium pyrophosphate, tetrasodium pyrophosphate, triethanolamine, triisopropanolamine, trisodium phosphate, tromethamine, urea, zinc carbonate hydroxide, zinc glycinate, and mixtures thereof. The pH increasing agent may be selected from the group consisting of ammonia, ammonium bicarbonate, ammonium carbonate, ammonium chloride, ammonium hydroxide, ammonium phosphate, calcium carbonate, calcium hydroxide, calcium oxide, diammonium phosphate, dipotassium phosphate, ethanolamine, isopropanolamine, isopropylamine, magnesium hydroxide, magnesium oxide, potassium borate, potassium carbonate, potassium citrate, potassium hydroxide, potassium oxide, sodium bicarbonate, sodium borate, sodium carbonate, sodium hydroxide, sodium sesquicarbonate, sodium silicate, urea, and mixtures thereof.

The total amount of cationic direct dyes and/or anionic direct dyes comprised in the first and/or the second compositions may be from 0.01% to 50%, or from 0.01% to 25%, or from 0.01% to 10%, or from 0.1% to 8%, by weight of the total composition.

Furthermore, the first and/or the second compositions may comprise all common additives known to be used in such preparations, for example perfume oils, complexing agents, waxes, preservatives, thickeners, alginates, guar gum, haircare substances, for example cationic polymers or lanolin derivatives, or anionic, nonionic, amphoteric or cationic surface-active substances. Amphoteric or nonionic surface-active substances may be used, for example betaine surfactants, propionates and glycinates, for example cocoamphoglycinates or cocoamphodiglycinates, ethoxylated surfactants with 1 to 1000 ethylene oxide units or with 1 to 300 ethylene oxide units, for example glyceride alkoxylates with, for example, 25 ethylene oxide units, ethoxylated castor oil, polyethylene glycol amides, ethoxylated alcohols, ethoxylated fatty alcohols (fatty alcohol alkoxylates) and ethoxylated sugar esters of fatty acids, particularly ethoxylated sorbitan fatty acid esters. The aforesaid constituents are used in amounts commonly employed for such purposes, for example the surface-active substances at a concentration of 0.1% to 30%, by weight of the total composition and the hair-care agents in an amount from 0.1% to 5% by weight of the total composition.

The first and/or the second compositions can be in the form of an aqueous or aqueous-alcoholic solution or a cream, gel, emulsion or aerosol foam. The first and/or the second composition can be in the form of a one-component preparation or in the form of a multicomponent preparation, for example in the form of a two-component preparation in which the direct dyes, e.g. the cationic and/or anionic direct dyes are packaged separately from the other constituents, and the ready-to-use first and/or second composition is prepared just before use by mixing the two compositions.

The first and/or the second compositions may be used with or without addition of a chemical oxidant.

The first and/or the second compositions may be used by applying to the hair an amount sufficient for the dyeing, usually 30 to 120 grams depending on the length of the hair, after which the compositions are allowed to act at about 15° C. to 45° C. for 1 to 60 minutes or 5 to 30 minutes. The hair is then thoroughly rinsed with water, optionally washed with a shampoo and then dried.

Moreover, the first and/or the second compositions may comprise natural or synthetic polymers or modified polymers of natural origin commonly used in cosmetic agents whereby the fixing and the dyeing of the hair are achieved at the same time. Such agents are generally referred to as tint fixatives or dye fixatives. Synthetic polymers that are known to be used for this purpose in the cosmetic field are, for example, polyvinylpyrrolidone, polyvinyl acetate and polyvinyl alcohol, or polyacrylate compounds such as polyacrylic acid or polymethacrylic acid, basic polymers of esters of polyacrylic acid, polymethacrylic acid and aminoalcohols, for example the salts or quaternization products thereof, polyacrylonitrile and polyvinyl acetate, as well as the copolymers of such compounds, for example polyvinylpyrrolidone-vinyl acetate. Natural polymers or modified natural polymers that are suitable for such use are, for example, chitosan (deacetylated chitin) or chitosan derivatives. The afore-said polymers can be contained in the first and/or second compositions in amounts commonly employed for such cosmetic agents, particularly in an amount from 1% to 5%, by weight of the composition. The pH of the tint fixative or dye fixative of the invention may be from 6 to 9.

The present description is not limited to the embodiments wherein only two different hair colouring compositions comprising direct dyes are applied to the hair, wherein the second hair colouring composition has a lower or higher pH than the first hair colouring composition. It may be envisaged to apply more than two different hair colouring compositions to the hair wherein each time the pH of the next composition is lower or higher than the pH of the previous composition.

Hair Colouring Kit

The present invention also relates to a hair colouring kit which may be used for carrying out the method for colouring hair described hereinbefore. The compositions comprised in the kit may comprise any of the ingredients disclosed hereinbefore in the present description.

The kit may comprise a first hair colouring composition and a second hair colouring composition, wherein each of the first and second compositions comprises one or more direct dyes and the pH of the second hair colouring composition is lower or higher than the pH of the first hair colouring composition.

Alternatively, the kit may comprise a first hair colouring composition comprising one or more direct dyes and a pH modifying agent, wherein the pH modifying agent is a pH reducing agent or a pH increasing agent.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for colouring hair comprising the steps of:
   i) providing a first hair colouring composition and a second hair colouring composition, wherein each of the first and second compositions comprises one or more direct dyes and the pH of the second hair colouring composition is lower or higher than the pH of the first hair colouring composition;
   ii) applying a portion or all of the first hair colouring composition to a first region of the hair;
   iii) applying a portion or all of the second hair colouring composition to a second region of the hair.

2. The method according to claim 1, wherein the method further comprises the step of:
   iv) rinsing the hair.

3. The method according to claim 1, wherein the second region is different from the first region.

4. The method according to claim 1, wherein the difference of pH between the first composition and the second composition is at least 0.1.

5. The method according to claim 1, wherein the difference of pH between the first composition and the second composition is at least 0.25.

6. The method according to claim 1, wherein the difference of pH between the first composition and the second composition is at least 0.5.

7. The method according to claim 1, wherein the first region is the hair roots and the second region is the hair lengths and tips.

8. The method according to claim 1, wherein the one or more direct dyes is selected from the group consisting of cationic direct dyes, anionic direct dyes, and mixtures thereof.

9. The method according to claim 8, wherein the cationic direct dyes are selected from the group consisting of Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Violet 2, 4-(3-(4-amino-9,10-dioxo-9,10-dihydroanthracen-1-ylamino)propyl)-4-methylmorpholin-4-ium -methylsulfate, (E)-1-(2-(4-(4,5-dimethylthiazol-2-yl)diazenyl)phenyl) (ethyl)aminolethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a, 10-tetrahydroanthracen-1-ylamino)-N-propylpropan-1-aminium bromide and mixtures thereof and the anionic direct dyes are selected from the group consisting of Acid Yellow 1, Acid Orange 3, Acid Black 1, Acid Black 52, Acid Orange 7, Acid Red 33, Acid Yellow 23, Acid Blue 9, Acid Violet 43, Acid Blue 62, Acid Blue 25, Acid Red 4, Acid Red 92, Acid Yellow 3, Acid Red 18, Acid Red 52, Acid Green 25, and mixtures thereof.

10. The method according to claim 1, wherein:
    in step ii), a first portion of the first composition is applied to the first region of the hair and a second portion of the first composition is retained and
    the method further comprises the step of adding a pH modifying agent to the second portion of the first composition to obtain the second composition.

11. The method according to claim 10, wherein the pH of the second hair colouring composition is lower than the pH of the first hair colouring composition and the pH modifying agent is a pH reducing agent.

12. The method according to claim 11, wherein the pH reducing agent is selected from the group consisting of acetic acid, acetyl mandelic acid, adipic acid, aluminum lactate, aluminum triformate, ammonium lactate, ammonium molybdate, ammonium nitrate, ammonium thiocyanate, ammonium vanadate, ascorbic acid, azelaic acid, babassu acid, bakuhan, benzilic acid, bismuth citrate, boric acid, calcium citrate, calcium dihydrogen phosphate, calcium phosphate, citric acid, diammonium citrate, dioleyl phosphate, disodium pyrophosphate, fumaric acid, galacturonic acid, glucoheptonic acid, glucuronic acid, glutaric acid, glycine, glycolic acid, glyoxylic acid, hydrobromic acid, hydrochloric acid, hydroxyethylpiperazine ethane sulfonic acid, isobutyric acid, lactic acid, lactobionic acid, magnesium glycinate, magnesium lactate, maleic acid, malic acid, malonic acid, maltobionic acid, metaphosphoric acid, monosodium citrate, mudstone powder, phenolsulfonphthalein, phenyl mercuric borate, phosphoric acid, phosphorus pentoxide, potassium bicarbonate, potassium biphthalate, potassium magnesium aspartate, potassium sodium tartrate, potassium tartrate, propane tricarboxylic acid, quinic acid, ribonic acid, sebacic acid, sodium aspartate, sodium bisulfate, sodium borate, sodium butoxyethoxy acetate, sodium calcium boron phosphate, sodium calcium copper phosphate, sodium calcium zinc phosphate, sodium citrate, sodium glycolate, sodium lactate, sodium phosphate, sodium succinate, succinic acid, sulfuric acid, tartaric acid, taurine,tea-hydroiodide, trisodium sulfosuccinate, triticum vulgare protein, triticum vulgare seed extract, uric acid, zinc hexametaphosphate, and mixtures thereof.

13. The method according to claim 11, wherein the pH reducing agent is selected from the group consisting of citric acid, phosphoric acid, salicylic acid, etidronic acid, acetic acid, ascorbic acid, hydrochloric acid, sulfuric acid, and mixtures thereof.

14. The method according to claim 11, wherein the pH of the first hair colouring composition is from 6 to 10 and the pH of the second hair colouring composition is from 2 to 8.

15. The method according to claim 10, wherein the pH of the second hair colouring composition is higher than the pH of the first hair colouring composition and the pH modifying agent is a pH increasing agent.

16. The method according to claim 15, wherein the pH increasing agent is selected from the group consisting of 1,6-hexanediamine, 2-aminobutanol, aminoethyl propanediol, aminomethyl propanediol, aminomethyl propanol, aminopropanediol, ammonia, ammonium bicarbonate, ammonium carbamate, ammonium carbonate, ammonium chloride, ammonium glycolate, ammonium hydroxide, ammonium phosphate, bis-hydroxyethyl tromethamine, butyl diethanolamine,calcium carbonate, calcium glycinate, calcium hydroxide, calcium oxide, copper glycinate, diammonium phosphate, dibutyl ethanolamine, diethyl ethanolamine, dimethyl isopropanolamine, dimethyl mea, dipotassium phosphate, disodium fumarate, disodium phosphate, disodium tartrate, ethanolamine, ethyl ethanolamine, guanidine carbonate, guanidine hcl, imidazole, isopropanolamine, isopropylamine, lithium carbonate, lithium hydroxide, magnesium hydroxide, magnesium oxide, methylethanolamine, pentapotassium triphosphate, pentasodium triphosphate, phenolsulfonphthalein, phenyl mercuric borate, potassium borate, potassium carbonate, potassium citrate, potassium hydroxide, potassium oxide, potassium phosphate, sesquiethoxytriethanolamine, sodium acetate, sodium aluminate, sodium aluminum lactate, sodium bicarbonate, sodium carbonate, sodium formate, sodium fumarate, sodium humate, sodium hydroxide, sodium metaphosphate, sodium metasilicate, sodium oxide, sodium sesquicarbonate, sodium silicate, sodium trimetaphosphate, strontium hydroxide, tea-diricinoleate/ipdi copolymer, tetrahydroxyethyl ethylenediamine, tetrapotassium pyrophosphate, tetrasodium pyrophosphate, triethanolamine, triisopropanolamine, trisodium phosphate, tromethamine, urea, zinc carbonate hydroxide, zinc glycinate, and mixtures thereof.

17. The method according to claim 15, wherein the pH increasing agent is selected from the group consisting of ammonia, ammonium bicarbonate, ammonium carbonate, ammonium chloride, ammonium hydroxide, ammonium phosphate, calcium carbonate, calcium hydroxide, calcium oxide, diammonium phosphate, dipotassium phosphate, ethanolamine, isopropanolamine, isopropylamine, magnesium hydroxide, magnesium oxide, potassium borate, potassium carbonate, potassium citrate, potassium hydroxide, potassium oxide, sodium bicarbonate, sodium borate, sodium carbonate, sodium hydroxide, sodium sesquicarbonate, sodium silicate, urea, and mixtures thereof.

18. The method according to claim 15, wherein the pH of the first hair colouring composition is from 2 to 8 and the pH of the second hair colouring composition is from 6 to 10.

19. A hair colouring kit comprising a first hair colouring composition and a second hair colouring composition, wherein each of the first and second compositions comprises one or more direct dyes and the pH of the second hair colouring composition is lower or higher than the pH of the first hair colouring composition.

* * * * *